(12) United States Patent
Jaeschke et al.

(10) Patent No.: US 9,328,090 B2
(45) Date of Patent: May 3, 2016

(54) ARYLETHYNYL DERIVATIVES

(71) Applicant: Hoffmann-La Roche Inc., Little Falls, NJ (US)

(72) Inventors: Georg Jaeschke, Basel (CH); Lothar Lindemann, Basel (CH); Heinz Stadler, Basel (CH); Eric Vieira, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 14/923,308

(22) Filed: Oct. 26, 2015

(65) Prior Publication Data

US 2016/0039787 A1   Feb. 11, 2016

Related U.S. Application Data

(63) Continuation of application No. 14/597,375, filed on Jan. 15, 2015, now abandoned, which is a continuation of application No. PCT/EP2013/064747, filed on Jul. 12, 2013.

(30) Foreign Application Priority Data

Jul. 17, 2012   (EP) ..................................... 12176662

(51) Int. Cl.
  *C07D 401/04* (2006.01)
  *C07D 209/52* (2006.01)
(52) U.S. Cl.
  CPC ............ *C07D 401/04* (2013.01); *C07D 209/52* (2013.01)

(58) Field of Classification Search
  CPC .................................................... C07D 401/04
  USPC ....................................... 546/276.7; 514/339
  See application file for complete search history.

(56) References Cited

FOREIGN PATENT DOCUMENTS

WO   2011/128279   * 10/2011

* cited by examiner

*Primary Examiner* — Patricia L Morris
(74) *Attorney, Agent, or Firm* — Tamara A. Kale

(57) ABSTRACT

The present invention relates to ethynyl derivatives of formula I

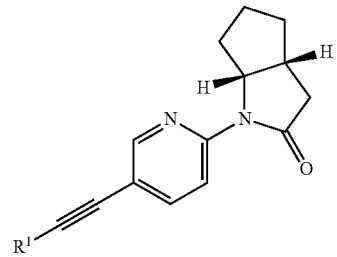

wherein
R¹ is phenyl, which is optionally substituted by 1-2 halogen atoms; selected from fluorine or chlorine;
or to a pharmaceutically acceptable acid addition salt in enantiomerically pure form.
It has been found that the compounds of general formula I are allosteric modulators of the metabotropic glutamate receptor subtype 5 (mGluR5).

5 Claims, No Drawings

ARYLETHYNYL DERIVATIVES

CROSS-REFERENCE TO RELATED APPLICATIONS

This application is a continuation of U.S. application Ser. No. 14/597,375, filed Jan. 15, 2015, which is a continuation of International Application No. PCT/EP2013/064747, filed Jul. 12, 2013, and claims priority to application EP 12176662.0, filed Jul. 17, 2012, each of which is incorporated herein by reference in its entirety.

The present invention relates to ethynyl derivatives of formula I

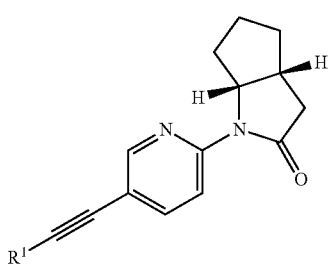

wherein
R$^1$ is phenyl, which is optionally substituted by 1-2 halogen atoms, selected from fluorine or chlorine;
or to a pharmaceutically acceptable acid addition salt, in enantiomerically pure form with the absolute configuration as shown in formula I.

It has now surprisingly been found that the compounds of general formula I are allosteric modulators of the metabotropic glutamate receptor subtype 5 (mGluR5) which show advantageous biochemical-, physicochemical- and pharmacodynamic-properties compared to compounds of prior art.

In the central nervous system (CNS) the transmission of stimuli takes place by the interaction of a neurotransmitter, which is sent out by a neuron, with a neuroreceptor.

Glutamate is the major excitatory neurotransmitter in the brain and plays a unique role in a variety of central nervous system (CNS) functions. The glutamate-dependent stimulus receptors are divided into two main groups. The first main group, namely the ionotropic receptors, forms ligand-controlled ion channels. The metabotropic glutamate receptors (mGluR) belong to the second main group and, furthermore, belong to the family of G-protein coupled receptors.

At present, eight different members of these mGluR are known and of these some even have sub-types. According to their sequence homology, signal transduction mechanisms and agonist selectivity, these eight receptors can be sub-divided into three sub-groups: mGluR1 and mGluR5 belong to group I, mGluR2 and mGluR3 belong to group II and mGluR4, mGluR6, mGluR7 and mGluR8 belong to group III.

Ligands of metabotropic glutamate receptors belonging to the first group can be used for the treatment or prevention of acute and/or chronic neurological disorders such as psychosis, epilepsy, schizophrenia, Alzheimer's disease, cognitive disorders and memory deficits, as well as chronic and acute pain.

Other treatable indications in this connection are restricted brain function caused by bypass operations or transplants, poor blood supply to the brain, spinal cord injuries, head injuries, hypoxia caused by pregnancy, cardiac arrest and hypoglycaemia. Further treatable indications are ischemia, Huntington's chorea, amyotrophic lateral sclerosis (ALS), tuberous sclerosis (TSC), dementia caused by AIDS, eye injuries, retinopathy, idiopathic parkinsonism or parkinsonism caused by medicaments as well as conditions which lead to glutamate-deficiency functions, such as e.g. muscle spasms, convulsions, migraine, urinary incontinence, nicotine addiction, opiate addiction, anxiety, vomiting, dyskinesia and depressions.

Disorders mediated full or in part by mGluR5 are for example acute, traumatic and chronic degenerative processes of the nervous system, such as Alzheimer's disease, senile dementia, Parkinson's disease, Huntington's chorea, amyotrophic lateral sclerosis and multiple sclerosis, psychiatric diseases such as schizophrenia and anxiety, depression, pain and drug dependency (*Expert Opin. Ther. Patents* (2002), 12, (12)).

A new avenue for developing selective modulators is to identify compounds which act through allosteric mechanism, modulating the receptor by binding to a site different from the highly conserved orthosteric binding site. Allosteric modulators of mGluR5 have emerged recently as novel pharmaceutical entities offering this attractive alternative. Allosteric modulators have been described, for example in WO2008/151184, WO2006/048771, WO2006/129199, WO2005/044797 and in particular WO2011/128279 as well as in *Molecular Pharmacology*, 40, 333-336, 1991; *The Journal of Pharmacology and Experimental Therapeutics*, Vol 313, No. 1, 199-206, 2005; *Nature*, 480 (7375), 63-68, 2012;

Described in the prior art are positive allosteric modulators. They are compounds that do not directly activate receptors by themselves, but markedly potentiate agonist-stimulated responses, increase potency and maximum of efficacy. The binding of these compounds increases the affinity of a glutamate-site agonist at its extracellular N-terminal binding site. Allosteric modulation is thus an attractive mechanism for enhancing appropriate physiological receptor activation. There is a scarcity of selective allosteric modulators for the mGluR5 receptor. Conventional mGluR5 receptor modulators typically lack drug safety, which lead to more side effects of the drug.

Therefore, there remains a need for compounds that overcome these deficiencies and that effectively provide selective allosteric modulators for the mGluR5 receptor. The present invention solved this problem, as seen below:

Comparison of Compounds of the Invention Versus Similar Compounds of Prior Art:

Structurally similar compounds of prior art have been disclosed in WO2011128279 (=Ref. 1, Hoffmann-La Roche) and the structurally most similar compounds of this patent (examples 13 40 and 59) are shown for comparison.

Comparison of Compounds of the Invention Vs. Reference Compounds Ex. 13, 40 and 59:

The compounds of the invention all have similar potencies compared to the reference compounds. Additionally they all show efficacies well below 60% compared to much higher values of the reference compounds (above 80%) which is a criteria with respect to tolerability issues of mGluR5 positive allosteric modulators. Compounds with high efficacy values above 60% show severe CNS related side-effects after oral dosing (seizures) at doses close to those where the desired therapeutic effects are observed (low therapeutic window). Compounds with efficacies below 60% are well tolerated at doses which may be 30 to 1000 times higher than the therapeutic dose while maintaining their desired therapeutic effects. Generally speaking, compounds of the present invention therefore have a clear advantage with respect to drug safety due to their efficacy values below 60% which correlates with the absence of severe CNS side-effect liabilities compared to structurally similar compounds of prior art.

LIST OF EXAMPLES

| Example | Structure | EC₅₀ (nM) mGlu5 PAM | Efficacy [%] |
|---|---|---|---|
| Ref. 1 Ex. 13 | 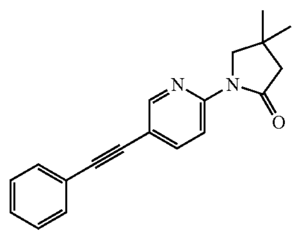 [SMILES: CC1(C)CC(=O)N(c2ccc(C#Cc3ccccc3)cn2)C1] | 37 | 129 |
| Ref. 1 Ex. 40 | 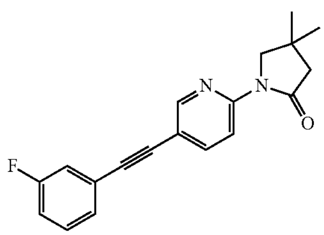 [SMILES: CC1(C)CC(=O)N(c2ccc(C#Cc3cccc(F)c3)cn2)C1] | 15 | 100 |
| Ref. 1 Ex. 59 | 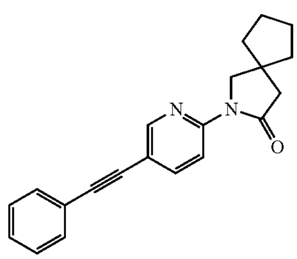 [SMILES: O=C1CC2(CCCC2)CN1c1ccc(C#Cc2ccccc2)cn1] | 16 | 81 |
| 1 | 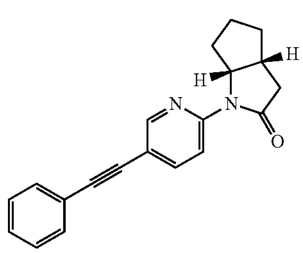 [SMILES: O=C1C[C@H]2CCC[C@H]2N1c1ccc(C#Cc2ccccc2)cn1] | 10 | 45 |
| 2 | 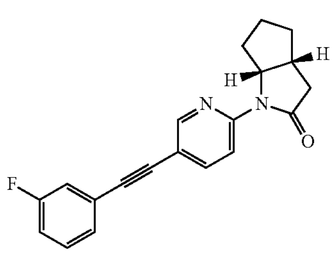 [SMILES: O=C1C[C@H]2CCC[C@H]2N1c1ccc(C#Cc2cccc(F)c2)cn1] | 10 | 48 |
| 3 | | 10 | 44 |
| 4 | | 8 | 19 |

Compounds of formula I are distinguished by having valuable therapeutic properties. They can be used in the treatment or prevention of disorders, relating to allosteric modulators for the mGluR5 receptor.

The most preferred indications for compounds which are allosteric modulators are schizophrenia and cognition.

The present invention relates to compounds of formula I and to their pharmaceutically acceptable salts, to these compounds as pharmaceutically active substances, to the processes for their production as well as to the use in the treatment or prevention of disorders, relating to allosteric modulators for the mGluR5 receptor, such as schizophrenia and cognition and to pharmaceutical compositions containing the compounds of formula I.

The following definitions of the general terms used in the present description apply irrespective of whether the terms in question appear alone or in combination.

As used herein, the term "halogen" denotes chlorine or fluorine.

The term "pharmaceutically acceptable salt" or "pharmaceutically acceptable acid addition salt" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

One embodiment of the invention are compounds of formula I-A

I-A wherein
R¹ is phenyl which is optionally substituted by 1-2 fluorine atoms;
or a pharmaceutically acceptable acid addition salt, in enantiomerically pure form with the absolute configuration as shown in formula I.

Compounds of formula I-A are the followings:
(3aR,6aR)-1-(5-(phenylethynyl)pyridin-2-yl)hexahydrocyclopenta[b]pyrrol-2(1H)-one
(3aR,6aR)-1-(5-((3-fluorophenyl)ethynyl)pyridin-2-yl)hexahydrocyclopenta[b]pyrrol-2(1H)-one
(3aR,6aR)-1-(5-((4-fluorophenyl)ethynyl)pyridin-2-yl)hexahydrocyclopenta[b]pyrrol-2(1H)-one
or
(3aR,6aR)-1-(5-((2,5-difluorophenyl)ethynyl)pyridin-2-yl)hexahydrocyclopenta[b]pyrrol-2(1H)-one.

The preparation of compounds of formula I of the present invention may be carried out in sequential or convergent synthetic routes. Syntheses of the compounds of the invention are shown in the following schemes 1 to 2. The skills required for carrying out the reaction and purification of the resulting products are known to those skilled in the art. The substituents and indices used in the following description of the processes have the significance given herein before.

The compounds of formula I can be manufactured by the methods given below, by the methods given in the examples or by analogous methods. Appropriate reaction conditions for the individual reaction steps are known to a person skilled in the art. The reaction sequence is not limited to the one displayed in the schemes, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

The present compounds of formula I and their pharmaceutically acceptable salts may be prepared by methods, known in the art, for example by the process variant described below, which process comprises a) reacting a compound of formula II

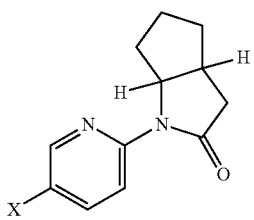

II wherein X is a halogen atom selected from bromine or iodine, and where the compound of formula II is a racemic mixture or in enantiomerically pure form with a suitable aryl-acetylene of formula III

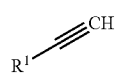

III to form a compound of formula I

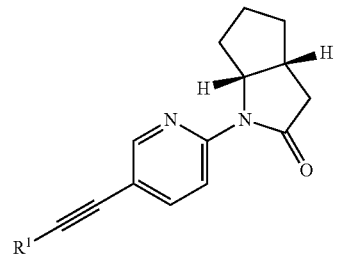

I wherein the substituents are described above, or if desired, converting the compounds obtained into pharmaceutically acceptable acid addition salts or b) reacting a compound of formula

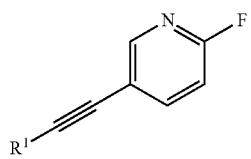

6 with a compound of formula

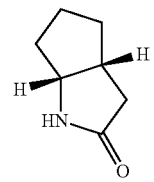

4

To a compound of formula

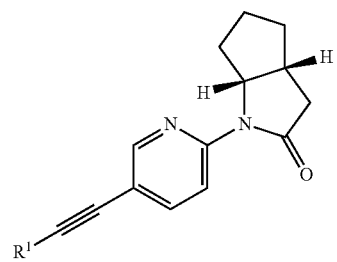

I wherein the substituents are described in claim 1, or if desired, converting the compounds obtained into pharmaceutically acceptable acid addition salts.

The preparation of compounds of formula I is further described in more detail in schemes 1 and 2 and in examples 1-4.

Scheme 1

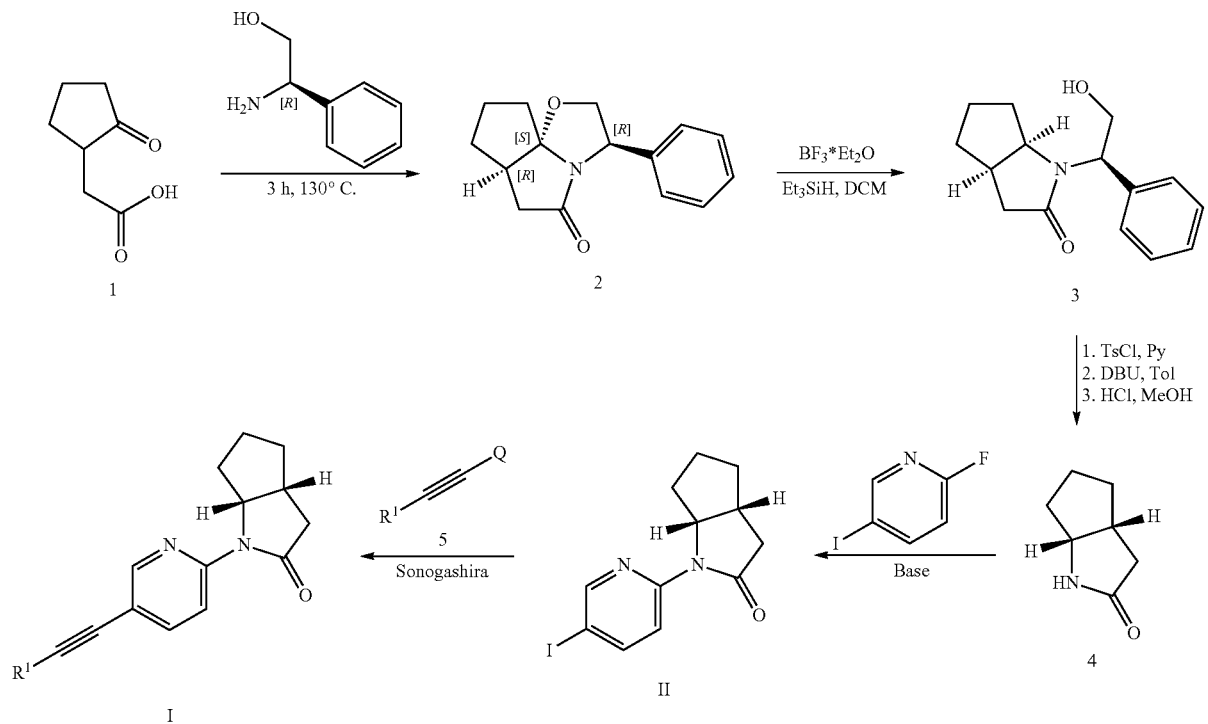

A halo-pyridine compound of formula II can be obtained by a base catalyzed reaction of an appropriate di-halogenated pyridine such as 2-fluoro-5-iodo-pyridine and an appropriate bicyclic urea of formula 4 (scheme 1). The compound of formula 4 can be obtained starting from racemic keto-acid of formula 1 by reaction with enantiomerically pure (R)-phenylalaninol to form the optically pure tricyclic intermediate 2 where all stereocenters are formed under complete stereocontrol using a procedure from M. Jida & al., Green Chem. 12, 961(2010). The tricyclic intermediate 2 is transformed into 4 using an analogous procedure to that described by Dubuffet & Lecouve in EP1354875 for a 6-membered carbocyclic ring analogue. Compound 2 is treated with borontrifluoride etherate under reductive conditions to form compound 3 (an N-benzyl-protected derivative of 4) which is de-protected via a chlorination-elimination sequence followed by hydrolysis of the enamine formed to yield enantiomerically pure bicyclic amide 4. Other synthetic procedures leading to racemic or enantiomerically pure 4 have also been published (J. Boivin & al., Tetrahedron, 51(23), 6517 (1995); S. Knapp; A. Levorse, J. Org. Chem. 53(17) 4006 (1988); Ishibashi, & al. Tet. Asym. 7(9), 2531 (1996)). Lactam 4 is then condensed with a dihalo pyridine such as 2-Fluoro-5-iodopyridine under base catalyzed conditions (NaH/DMF; or $Cs_2CO_3$/Toluene) to form a compound of formula II where X is iodine. Reaction of lactam 4 with a dihalopyridine such as 2-iodo-5-bromopyridine using Palladium catalyzed reaction conditions (Buchwald) can also form a compound of formula II where X is bromine. Compound II is then reacted with an appropriately substituted arylacetylene derivative 5 (where Q is either hydrogen or an in-situ cleavable protecting group such as a trialkylsilyl- or aryldialkylsilyl-group, preferably hydrogen or trimethylsilyl) under Palladium catalyzed coupling conditions (Sonogashira reaction) to form compounds of formula I. In the case where racemic 4 is used, the enantiomers can be separated at any given stage during the synthesis of compounds of formula I using procedures known to persons skilled in the art.

It is also possible to invert the sequence of reactions leading to compounds of formula I (scheme 2). In this case, the Sonogashira reaction between the arylacetylene derivative 5 and the dihalo-pyridine is performed first to yield an arylacetylene-pyridine compound of formula 6 which is then condensed with bicyclic lactam 4 to yield compounds of formula I.

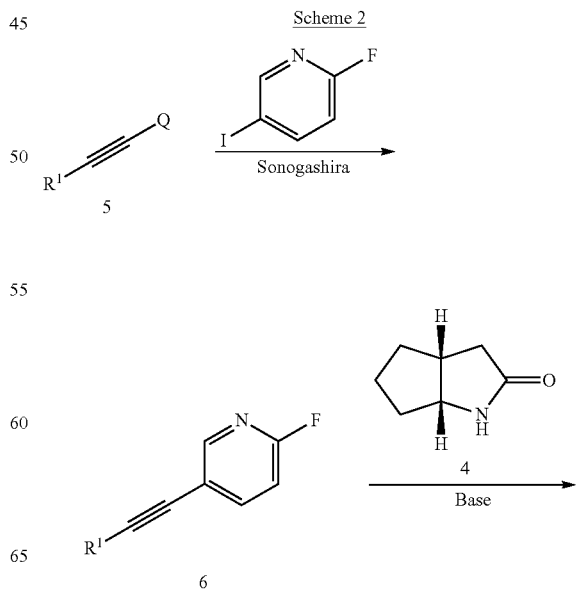

Scheme 2

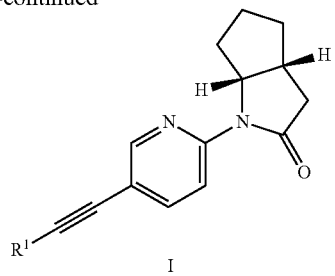

The compound of formula I as described herein as well as its pharmaceutically acceptable salt is used in the treatment or prevention of psychosis, epilepsy, schizophrenia, Alzheimer's disease, cognitive disorders and memory deficits, chronic and acute pain, restricted brain function caused by bypass operations or transplants, poor blood supply to the brain, spinal cord injuries, head injuries, hypoxia caused by pregnancy, cardiac arrest and hypoglycaemia, ischemia, Huntington's chorea, amyotrophic lateral sclerosis (ALS), dementia caused by AIDS, eye injuries, retinopathy, idiopathic parkinsonism or parkinsonism caused by medicaments, muscle spasms, convulsions, migraine, urinary incontinence, gastrointestinal reflux disorder, liver damage or failure whether drug or disease induced, Fragile-X syndrom, Down syndrom, autism, nicotine addiction, opiate addiction, anxiety, vomiting, dyskinesia, eating disorders, in particular bulimia or anorexia nervosa, and depressions, particularly for the treatment and prevention of acute and/or chronic neurological disorders, anxiety, the treatment of chronic and acute pain, urinary incontinence and obesity.

The preferred indications are schizophrenia and cognitive disorders.

Present invention further relates to the use of a compound of formula I as described herein, as well as its pharmaceutically acceptable salt, for the manufacture of a medicament, preferably for the treatment and prevention of the above-mentioned disorders.

Biological Assays and Data

Intracellular $Ca^{2+}$ Mobilization Assay

A monoclonal HEK-293 cell line stably transfected with a cDNA encoding for the human mGlu5a receptor was generated; for the work with mGlu5 Positive Allosteric Modulators (PAMs), a cell line with low receptor expression levels and low constitutive receptor activity was selected to allow the differentiation of agonistic versus PAM activity. Cells were cultured according to standard protocols (Freshney, 2000) in Dulbecco's Modified Eagle Medium with high glucose supplemented with 1 mM glutamine, 10% (vol/vol) heat-inactivated bovine calf serum, Penicillin/Streptomycin, 50 µg/ml hygromycin and 15 µg/ml blasticidin (all cell culture reagents and antibiotics from Invitrogen, Basel, Switzerland).

About 24 hrs before an experiment, $5 \times 10^4$ cells/well were seeded in poly-D-lysine coated, black/clear-bottomed 96-well plates. The cells were loaded with 2.5 µM Fluo-4AM in loading buffer (1×HBSS, 20 mM HEPES) for 1 hr at 37° C. and washed five times with loading buffer. The cells were transferred into a Functional Drug Screening System 7000 (Hamamatsu, Paris, France), and 11 half logarithmic serial dilutions of test compound at 37° C. were added and the cells were incubated for 10-30 min. with on-line recording of fluorescence. Following this pre-incubation step, the agonist L-glutamate was added to the cells at a concentration corresponding to $EC_{20}$ (typically around 80 µM) with on-line recording of fluorescence; in order to account for day-to-day variations in the responsiveness of cells, the $EC_{20}$ of glutamate was determined immediately ahead of each experiment by recording of a full dose-response curve of glutamate.

Responses were measured as peak increase in fluorescence minus basal (i.e. fluorescence without addition of L-glutamate), normalized to the maximal stimulatory effect obtained with saturating concentrations of L-glutamate. Graphs were plotted with the % maximal stimulatory using XLfit, a curve fitting program that iteratively plots the data using Levenburg Marquardt algorithm. The single site competition analysis equation used was $y=A+((B-A)/(1+((x/C)D)))$, where y is the % maximal stimulatory effect, A is the minimum y, B is the maximum y, C is the $EC_{50}$, x is the log 10 of the concentration of the competing compound and D is the slope of the curve (the Hill Coefficient). From these curves the $EC_{50}$ (concentration at which half maximal stimulation was achieved), the Hill coefficient as well as the maximal response in % of the maximal stimulatory effect obtained with saturating concentrations of L-glutamate were calculated.

Positive signals obtained during the pre-incubation with the PAM test compounds (i.e. before application of an $EC_{20}$ concentration of L-glutamate) were indicative of an agonistic activity, the absence of such signals were demonstrating the lack of agonistic activities. A depression of the signal observed after addition of the $EC_{20}$ concentration of L-glutamate was indicative of an inhibitory activity of the test compound.

In the list of examples below are shown the corresponding results for compounds which all have $EC_{50}$ values less or equal 10 nM.

| Example | $EC_{50}$ (nM) mGlu5 PAM |
|---------|--------------------------|
| 1 | 10 |
| 2 | 10 |
| 3 | 10 |
| 4 | 8 |

The compounds of formula (I) and pharmaceutically acceptable salts thereof can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. However, the administration can also be effected rectally, e.g. in the form of suppositories, or parenterally, e.g. in the form of injection solutions.

The compounds of formula (I) and pharmaceutically acceptable salts thereof can be processed with pharmaceutically inert, inorganic or organic carriers for the production of pharmaceutical preparations. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like; depending on the nature of the active substance no carriers are, however, usually required in the case of soft gelatine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula (I), but as a rule are not necessary. Suitable carriers for suppositories are, for example, natural or hardened oils, waxes, fats, semi-liquid or liquid polyols and the like.

In addition, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

As mentioned earlier, medicaments containing a compound of formula (I) or pharmaceutically acceptable salts thereof and a therapeutically inert excipient are also an object of the present invention, as is a process for the production of such medicaments which comprises bringing one or more compounds of formula I or pharmaceutically acceptable salts thereof and, if desired, one or more other therapeutically valuable substances into a galenical dosage form together with one or more therapeutically inert carriers.

As further mentioned earlier, the use of the compounds of formula (I) for the preparation of medicaments useful in the prevention and/or the treatment of the above recited diseases is also an object of the present invention.

The dosage can vary within wide limits and will, of course, be fitted to the individual requirements in each particular case. In general, the effective dosage for oral or parenteral administration is between 0.01-20 mg/kg/day, with a dosage of 0.1-10 mg/kg/day being preferred for all of the indications described. The daily dosage for an adult human being weighing 70 kg accordingly lies between 0.7-1400 mg per day, preferably between 7 and 700 mg per day.

Preparation of Pharmaceutical Compositions Comprising Compounds of the Invention Tablets of the following composition are produced in a conventional manner:

| | mg/Tablet |
|---|---|
| Active ingredient | 100 |
| Powdered. lactose | 95 |
| White corn starch | 35 |
| Polyvinylpyrrolidone | 8 |
| Na carboxymethylstarch | 10 |
| Magnesium stearate | 2 |
| Tablet weight | 250 |

Example 1

(3aR,6aR)-1-(5-(phenylethynyl)pyridin-2-yl)hexahydrocyclopenta[b]pyrrol-2(1H)-one

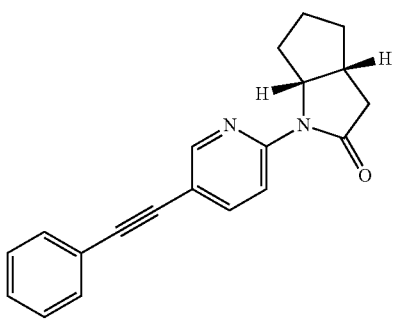 [SMILES: O=C1C[C@H]2CCC[C@H]2N1c1ccc(C#Cc2ccccc2)cn1]

Step 1: (1S,5aR)—(R)-3-Phenyl-hexahydro-1-oxa-3a-aza-cyclopenta[c]pentalen-4-one

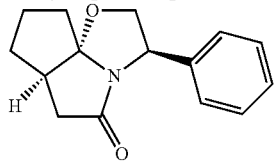 [SMILES: O=C1C[C@H]2CCC[C@]23OC[C@@H](c2ccccc2)N13]

A mixture of (rac)-2-(2-oxocyclopentyl)acetic acid (1030 mg, 7.25 mmol) and (R)-2-amino-2-phenylethanol (994 mg, 7.25 mmol) in a 20 ml closed tube was heated for 3 h at 130° C. and allowed to cool to room temperature. The residue was taken up in 50 ml of dichloromethane. The organic phase was washed once with 10 ml 1N HCl solution and once with 10 ml saturated NaHCO$_3$ solution. After drying over magnesium sulfate and concentration in vaccuo, one obtains 1.6 g (91%) of almost pure title compound as a light brown oil which was directly used in the next step MS: m/e=244.0 (M+H$^+$).

Step 2: (R)-1-((R)-Hydroxy-1-(R)-phenethyl)-hexahydro-cyclopenta[b]pyrrol-2-one

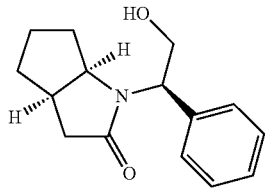 [SMILES: O=C1C[C@H]2CCC[C@H]2N1[C@@H](CO)c1ccccc1]

To a solution of (1S,5aR)—(R)-3-phenyl-hexahydro-1-oxa-3a-aza-cyclopenta[c]pentalen-4-one (1.6 g, 6.58 mmol) in dichloromethane (10 ml) was added boron trifluoride etherate (5.6 g, 5.00 ml, 39.5 mmol, 6.0 equiv.) and triethylsilane (1.53 g, 2.1 ml, 13.2 mmol, 2.0 equiv.). After stirring for 20 h at 50° C. the reaction was allowed to warm up to room temperature and the pH was adjusted to 7 by addition of 5% NaHCO$_3$ solution. After extraction with dichloromethane, water, drying and concentration in vaccuo, one obtains the almost pure title compound, (1.6 g, 99%), as a light brown oil which was directly used in the next step MS: m/e=246.2 (M+H$^+$).

Step 3: (R)-1-((R)-Chloro-1-(R)-phenethyl)-hexahydro-cyclopenta[b]pyrrol-2-one

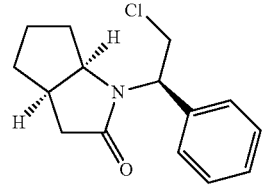 [SMILES: O=C1C[C@H]2CCC[C@H]2N1[C@@H](CCl)c1ccccc1]

To a solution of (3aR,6aR)-1-((R)-2-hydroxy-1-phenylethyl)hexahydrocyclopenta[b]pyrrol-2(1H)-one (1.6 g, 6.52 mmol) in dichloromethane (10 ml) was added pyridine (929 mg, 950 µl, 11.7 mmol). The solution was then cooled to 0° C. and p-toluenesulfonyl chloride (1.49 g, 7.83 mmol, 1.2 equiv.) was added in portions over a 5 min period. After stirring for 30 min at 5° C. the reaction was allowed to warm up to room temperature and stirred for another 20 min. After extraction with dichloromethane/water, standard workup and concentration in vaccuo, one obtains 1.59 g of crude material which was then dissolved in 50 ml of dichloromethane to which ca. 15 g of silica gel were added. After stirring for 5 min, the solvent was evaporated. The residue was suspended in dichloromethane. The solids were filtered off and washed three times with 20 ml of a 1:1 mixture of dichloromethane and ethyl acetate. The filtrate was concentrated in vaccuo to yield 1.45 g (84%) of almost pure title compound as a light brown oil which was directly used in the next step MS: m/e=264.1, 266.2 (M+H$^+$).

Step 4: (3aR,6aR)-1-(1-phenylvinyl)hexahydrocyclopenta[b]pyrrol-2(1H)-one

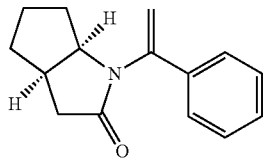 [SMILES: C=C(c1ccccc1)N1C(=O)C[C@H]2CCC[C@H]21]

A solution of (R)-1-((R)-chloro-1-(R)-phenethyl)-hexahydro-cyclopenta[b]pyrrol-2-one (1.4 g, 5.31 mmol) in 20 ml of toluene was treated with DBU (1.01 g, 1.00 ml, 6.63 mmol, 1.25 equiv.) The reaction was refluxed for 2 h, concentrated in vaccuo, extracted with ethyl acetate/water, dried and concentrated in vaccuo to yield 1.19 g (99%) of title compound as a light brown oil, MS: m/e=228.3 (M+H$^+$), which was directly used in the next step.

Step 5: (−)-(R)-Hexahydro-cyclopenta[b]pyrrol-2-one

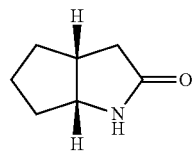

To a solution of (3aR,6aR)-1-(1-phenylvinyl)hexahydrocyclopenta[b]pyrrol-2(1H)-one (1.2 g, 5.28 mmol) in 5 ml of methanol was added 4M HCl solution (7.92 ml, 31.7 mmol, 6.0 equiv.) and the reaction was stirred for 1 h at room temperature. The pH of the reaction was adjusted to 7 by addition of 4M NaOH solution (ca. 8 ml), ether (20 ml) was added and the aqueous phase was saturated with sodium chloride and extracted twice with ethyl acetate. After drying over magnesium sulfate and concentration in vaccuo, one obtains 1.0 g of a light yellow oil containing product and acetophenone. After purification by flash chromatography over silica gel (20 g) using a 20% to 100% ethyl acetate in heptane gradient followed by elution with 2% MeOH in ethyl acetate yielded 0.66 g (53%) of title compound as a light yellow solid, the NMR data of which corresponded exactly to that reported in the literature. The material was directly used in the next step.

Step 6: (3aR,6aR)-1-(5-iodopyridin-2-yl)hexahydrocyclopenta[b]pyrrol-2(1H)-one

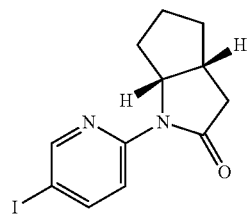 [SMILES: O=C1C[C@H]2CCC[C@H]2N1c1ccc(I)cn1]

To a solution of (3aR,6aR)-hexahydrocyclopenta[b]pyrrol-2(1H)-one (210 mg, 1.68 mmol) and 2-fluoro-5-iodopyridine (412 mg, 1.85 mmol, 1.1 equiv.) in toluene (1.1 ml) were added Cs$_2$CO$_3$ (656 mg, 2.01 mmol, 1.2 equiv.) The reaction was stirred for 16 h at 105° C. The residue was taken up in ethyl acetate, the solids were filtered off and washed with ethyl acetate. The filtrate was concentrated in vaccuo and the residue was purified by flash chromatography (SiO$_2$, 20 g) using a 0% to 60% ethyl acetate in heptane gradient. One obtains the title compound, (300 mg 55%), as a colorless oil, MS: m/e=329.4 (M+H$^+$).

Step 7: (−)-(3aR,6aR)-1-(5-(phenylethynyl)pyridin-2-yl)hexahydrocyclopenta[b]pyrrol-2(1H)-one In a 10 ml Pyrex tube were dissolved (3aR,6aR)-1-(5-iodopyridin-2-yl)hexahydro-cyclopenta[b]pyrrol-2(1H)-one (107 mg, 326 μmol) in 2 ml of THF. Argon was bubbled through the solution. Ethynylbenzene (59.9 mg, 64.5 μl, 587 μmol, 1.8 equiv.), triethylamine (99.0 mg, 136 μmol, 978 μmol, 3.0 equiv.), bis(triphenylphosphine)palladium(II) chloride (13.7 mg, 19.6 μmol, 0.06 equiv.), triphenylphosphine (1.71 mg, 6.52 μmol, 0.02 equiv.), and copper (I) iodide (1.86 mg, 9.78 μmol, 0.03 equiv.) were added. The dark brown solution was stirred at 50° C. for 2 h. The residue was taken up in ethyl acetate, the solids were filtered off and washed with ethyl acetate. The filtrate was concentrated in vaccuo and the residue was purified by flash chromatography (SiO$_2$, 20 g) using a 0% to 60% ethyl acetate in heptane gradient. One obtained 95 mg (96%) of the title compound as a viscous yellow oil, MS: m/e=303.2 (M+H$^+$).

Example 2

(3aR,6aR)-1-(5-((3-Fluorophenyl)ethynyl)pyridin-2-yl)hexahydrocyclopenta[b]pyrrol-2(1H)-one

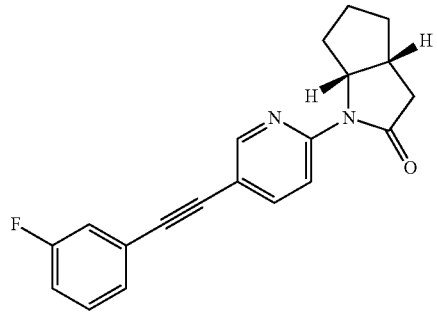 [SMILES: O=C1C[C@H]2CCC[C@H]2N1c1ccc(C#Cc2cccc(F)c2)cn1]

The title compound was prepared in accordance with the general method of Example 1, step 7 using (3aR,6aR)-1-(5-iodopyridin-2-yl)hexahydro-cyclopenta[b]pyrrol-2(1H)-one (107 mg, 0.326 mmol) (Example 1, step 6) and 1-ethynyl-3-fluorobenzene to yield 100 mg (96%) of the title compound as a viscous yellow oil; MS: m/e=321.2 (M+H$^+$).

Example 3

(3aR,6aR)-1-(5-((4-Fluorophenyl)ethynyl)pyridin-2-yl)hexahydrocyclopenta[b]pyrrol-2(1H)-one

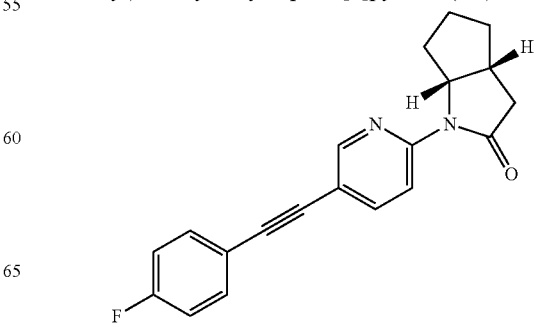

The title compound was prepared in accordance with the general method of Example 1, step 7 using (3aR,6aR)-1-(5-iodopyridin-2-yl)hexahydro-cyclopenta[b]pyrrol-2(1H)-one (100 mg, 0.305 mmol) (Example 1, step 6) and 1-ethynyl-4-fluorobenzene to yield 75 mg (77%) of the title compound as a viscous yellow oil; MS: m/e=321.2 (M+H$^+$).

Example 4

(3aR,6aR)-1-(5-((2,5-Difluorophenyl)ethynyl)pyridin-2-yl)hexahydrocyclopenta[b]pyrrol-2(1H)-one

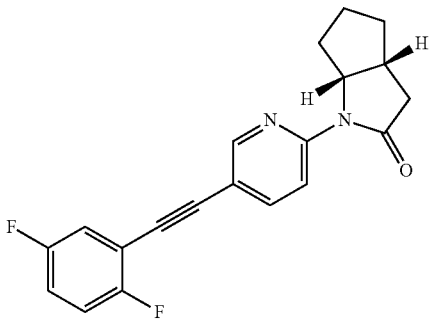 [SMILES: O=C1C[C@H]2CCC[C@H]2N1c1ccc(C#Cc2cc(F)ccc2F)cn1]

The title compound was prepared in accordance with the general method of Example 1, step 7 using (3aR,6aR)-1-(5-iodopyridin-2-yl)hexahydro-cyclopenta[b]pyrrol-2(1H)-one (140 mg, 0.427 mmol) (Example 1, step 6) and 1-ethynyl-2,5-difluorobenzene to yield 142 mg (98%) of the title compound as a viscous light brown oil; MS: m/e=339.5 (M+H$^+$).

The invention claimed is:
1. An ethynyl derivative of formula I

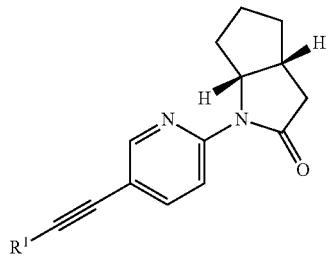

I wherein

R$^1$ is phenyl, which is optionally substituted by 1-2 halogen atoms, selected from fluorine or chlorine;

or a pharmaceutically acceptable acid addition salt in enantiomerically pure form.

2. An ethynyl derivative of formula I-A according to claim 1

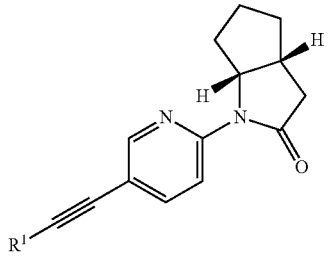

I-A wherein

R$^1$ is phenyl which is optionally substituted by 1-2 fluorine atoms;

or a pharmaceutically acceptable acid addition salt in enantiomerically pure form.

3. A compound of formula I according to claim 1, wherein the compound is (3aR,6aR)-1-(5-(phenylethynyl)pyridin-2-yl)hexahydrocyclopenta[b]pyrrol-2(1H)-one (3aR,6aR)-1-(5-((3-fluorophenyl)ethynyl)pyridin-2-yl)hexahydrocyclopenta[b]pyrrol-2(1H)-one (3aR,6aR)-1-(5-((4-fluorophenyl)ethynyl)pyridin-2-yl)hexahydrocyclopenta[b]pyrrol-2(1H)-one or (3aR,6aR)-1-(5-((2,5-difluorophenyl)ethynyl)pyridin-2-yl)hexahydrocyclopenta[b]pyrrol-2(1H)-one.

4. A pharmaceutical composition comprising at least one of the compounds according to claim 1 as well as its pharmaceutically acceptable salt.

5. The composition of claim 4, wherein the compound is present as in mixtures of enantiomers, diastereomers, or in enantiomerically pure form; as well as its pharmaceutically acceptable salt.

* * * * *